United States Patent [19]
Nakamura et al.

[11] Patent Number: 5,518,999
[45] Date of Patent: May 21, 1996

[54] METHOD FOR TREATING KAPOSI'S SARCOMA AND BLOCKING OR INHIBITING VASCULAR PERMEABILITY

[75] Inventors: Shuji Nakamura, Pasadena, Calif.; Robert C. Gallo, Bethesda, Md.; Yasuaki Osada, Tokyo, Japan; Shinsaku Sakurada, Tokyo, Japan; Noriko G. Tanaka, Tokyo, Japan; Syed Z. Salahuddin, Pasadena, Calif.

[73] Assignees: The United States of America as represented by the Secretary of the Department of Health and Human Services, Washington, D.C.; Daiichi Pharmaceutical Co., Ltd., Tokyo, Japan

[21] Appl. No.: 336,612

[22] Filed: Nov. 9, 1994

Related U.S. Application Data

[63] Continuation of Ser. No. 810,420, Dec. 20, 1991, abandoned.

[51] Int. Cl.⁶ .................................................... A61K 38/16
[52] U.S. Cl. ............................................. 514/8; 530/395
[58] Field of Search .................................. 514/8; 500/395

Primary Examiner—Howard E. Schain
Attorney, Agent, or Firm—Townsend and Townsend and Crew

[57] ABSTRACT

The present invention is directed to a method for arresting or inhibiting the growth of cells in Kaposi's Sarcoma lesions and a method for arresting or inhibiting the growth of the Kaposi's Sarcoma lesions, said methods comprising contacting the cells in the lesions with an effective amount of SP-PG, a naturally occurring sulfated polysaccharide-peptidoglycan produced by a specific species of the bacterium Arthrobacter, AT-25. The invention is also directed to blocking or inhibiting the activity of cellular vascular permeability factor(s), which comprises contacting vascular cells with an effective amount of SP-PG. In one embodiment, there is provided a method for blocking or inhibiting increased vascular permeability (and resulting edema) in diseases and disorders in which the increased vascular permeability contributes to the pathology, for example, in Kaposi's Sarcoma, tumorigenesis, inflammation, diabetic retinopathy, etc. Increased effectiveness is obtained when SP-PG is combined with cortisone or a cortisone derivative, such as hydrocortisone or tetrahydrocortisone.

5 Claims, 19 Drawing Sheets

METHOD FOR TREATING KAPOSI'S SARCOMA AND BLOCKING OR INHIBITING VASCULAR PERMEABILITY

This is a continuation of application Ser. No. 07/810,420 filed Dec. 20, 1991, now abandoned.

BACKGROUND OF THE INVENTION

1. Field of the Invention

The present invention is directed to a method for arresting or inhibiting the growth of malignant or premalignant cells in Kaposi's Sarcoma lesions. The invention is further directed to a method of blocking or inhibiting the activity of cellular vascular permeability factor or factors in vascular cells.

2. Background Information

Various forms of Kaposi's Sarcoma are clinically recognized. These include classical [W. A. Reynolds et al. *Medicine* 44, 419 (1965)], African endemic [J. F. Taylor et al. *Br. J. Cancer* 26, 483 (1972)], immunosuppressive therapy-associated [I. Penn *Transplantation* 27, 8-11 (1979); D. I. Greenfield et al. *J. Rheumatol.* 13, 637 (1986)], and an aggressive form of Kaposi's Sarcoma frequently observed in young HIV-1 infected homosexual men [K. B. Hymes et al. *Lancet* ii, 598 (1981); B. Safai al. *Ann. Intern. Med.* 103, 744 (1985)]. Despite the clinical and epidemiological distinct forms, all are histologically similar, and exhibit microvascular proliferation (angiogenesis) in the initial stage of lesion development, which is soon followed by the presence of proliferating spindle cells, edema, and infiltration by multiple cell types [N. S. McNutt et al. *Am. J. Pathol.* 111, 62 (1983)].

The present inventors have previously developed in vitro systems for the long-term culture of Kaposi's Sarcoma-derived spindle shaped cells using conditioned media from HTLV-I or HTLV-II infected and immortalized CD4 positive T cells or from activated peripheral blood mononuclear cells, to facilitate cell growth [S. Nakamura et al. *Science* 242, 426 (1988)] and in vivo systems which simulate the formation of Kaposi's Sarcoma [S. Nakamura et al. *Science* 242, 426 (1988); S. Z. Salahuddin et al. *Science* 242, 430 (1988)]. These cells produce several lymphokines which establish the in vitro growth of these cells. They include interleukin 6 (IL-6) [S. A. Miles et al. *Proc. Natl. Acad. Sci. USA* 87, 4068 (1990)], interleukin 1 (IL-1), and tumor necrosis factor $\alpha$ (TNFe) [S. Nakamura et al. *Science* 242, 426 (1988)]. However, the most active growth factor for the Kaposi's Sarcoma spindle cells is a 30 kD protein [S. Nakamura et al. *Science* 242, 426 (1988)] recently purified and now under analysis. The effect of the 30 kD lymphokine is augmented by corticosteroids, but the mechanism for this interaction is unknown. In addition to these T cell-derived lymphokines, one viral protein, the HIV-1 regulatory protein called Tat, has also been shown to have similar growth promoting effects on these cells [B. Ensoli et al. *Nature* 345, 84 (1990)], and its effect is at very low concentrations.

These cultured Kaposi's Sarcoma spindle cells obtained from different patients and from various tissues/organs themselves produce various cytokines which affect their own growth, growth of other cells, and other effects which lead to biological changes resembling Kaposi's Sarcoma. These cytokines include: basic fibroblast growth factor (bFGF)-like factor, platelet-derived growth factor (PDGF), IL-1, granulocyte-monocyte colony stimulating factor (GM-CSF) [B. Ensoli et al. *Science* 243, 223 (1989)], IL-6 IS. A. Miles et al. *Proc. Natl. Acad. Sci. USA* 87, 4068 (1990)], and a vascular permeability factor(s). The cultured human Kaposi's Sarcoma cells induce vascularization on chicken chorio-allantoic membranes (CAM), and when transplanted into nude mice they induce vascular hyperpermeability and resultant edema, angiogenesis, and the development of Kaposi's Sarcoma-like lesions of murine origin [S. Z. Salahuddin et al. *Science* 242, 430 (1988)]. These results combined with some clinical observations suggest that Kaposi's Sarcoma is not a simple malignancy, but at least in its early stages is more likely a reactive lesion, developing in response to endogenous soluble mediators [J. Costa and A. S. Rabson *Lancet* i, 58 (1983); J. J. Brooks *Lancet* ii, 1309 (1986)].

Kaposi's Sarcoma is currently treated with various cytotoxic agents such as vinblastine, bleomycin [P. A. Volberding et al. *Ann. Intern. Med.* 103, 335 (1985); P. Gill et al. *Am. J. Oncol.* 13, 315 (1990)], suramin [A.M. Levine et al. *Ann. Intern. Med.* 105, 32 (1986)], or with cytokines such as interferon $\alpha$ (IFN$\alpha$) [S. E. Krown et al. *N. Engl. J. Med.* 308, 1071 (1983)]. Both of these forms of therapy may affect many cell functions. More recently an angiostatic compound, pentosan polysulfate, has also been employed, but many recently described potential angiostatic compounds [R. C. Gallo *Quatrieme Colloque Des Cent Gardes* (Proceedings, Biomedical Research Strategy on AIDS) 113 (1989); B. Ensoliet al. *Hematol. Oncol. Clin. North Am.* 5, 281 (1991); S. Taylor and S. Folkman *Nature* 297, 307 (1982); J. Folkman et al. *Science* 243, 1490 (1989); Jo Folkman and D. E. Ingber *Ann. Surg.* 206, 374 (1987); T. E. Maione et al. *Science* 247, 77 (1990)] still remain to be clinically tested. One of these was the compound of the present invention, SP-PG, a naturally occurring sulfated polysaccharide-peptidoglycan produced by a specific species of the bacterium Arthrobacter, AT-25. SP-PG has been reported to inhibit the development of vascularization in CAM assays and the growth of subcutaneously inoculated solid tumors (which require angiogenesis for their growth), while not affecting growth of ascites tumor cells of the same origin [N. Tanaka et al. *Cancer Res.* 49, 6726 (1989)].

SP-PG is also known as DF4639. U.S. Pat. No. 4,900,815 (the entire disclosure of which is hereby incorporated by reference) describes the anti-tumor and anti-angiogenic effects of DF4639. However, previous to the present invention, the ability of this drug to arrest or inhibit the growth of cells in Kaposi's Sarcoma lesions and the ability of SP-PG to arrest or inhibit the growth of the lesions themselves were not known or suspected. Likewise, the ability of SP-PG to block or inhibit the activity of cellular vascular permeability factors was neither known nor suspected.

Although the anti-angiogenesis activity and the anti-tumor activity of SP-PG were both previously described in U.S. Pat. No. 4,900,815, the previous inventors did not test the drug on Kaposi's Sarcoma or suggest that it might inhibit the growth of Kaposi's Sarcoma lesions. It is believed that this is due, in part, to the fact that the patent deals with the effect of SP-PG on solid tumors and the Kaposi's Sarcoma lesion is not considered to be a "classical" solid tumor. It is not comprised entirely of tumor cells; normal cells of various types are present in Kaposi's Sarcoma lesions. In any event, it was not obvious to the scientists skilled in the art who were familiar with the activities of DF 4639 (SP-PG) that the drug would inhibit development of Kaposi's Sarcoma lesions. Nor did these scientists foresee that it should even be proposed as a possible treatment for Kaposi's Sarcoma.

Therefore, with respect to its antitumor and antiangiogenic activities, the present inventors were the first to realize the use of the drug in the treatment of Kaposi's Sarcoma patients. Furthermore, there was no indication from previously obtained data using the drug that it affected vascular permeability.

The present inventors were able to demonstrate that the edema sometimes associated with Kaposi's sarcoma (KS) in patients could be induced by AIDS-KS cells inoculated subcutaneously into nude mice. This effect of the KS cells had not previously been demonstrated. The present inventors were then able to demonstrate that DF 4639 (SP-PG) could block this activity. Since cellular mechanisms involved in inducing or blocking angiogenesis are not well understood and since mechanisms involved in inducing or blocking vascular permeability are not well understood, there was no reason to suspect a common mechanism of induction of angiogenesis or blocking increased vascular permeability and no reason to assume that a drug that inhibited angiogenesis would also block the increased vascular permeability which leads to edema.

Since the anti-angiogenic activity of SP-PG responsible for an anti-tumor effect was believed to target cells of vascular origin [N. Tanaka et al. *Cancer Res.* 49, 6726 (1989)], the present inventors initiated tests of SP-PG in in vitro and in vivo Kaposi's Sarcoma systems developed at the National Cancer Institute (NCI) [S. Nakamura et al. *Science* 242, 426 (1988); S. Z. Salahuddin et al. *Science* 242, 430 (1988)]. Human recombinant interferon α (IFNα) [S. E. Krown et al. *N. Engl. J. Med.* 308, 1071 (1983)], suramin [A.M. Levine et al. *Ann. Intern. Med.* 105, 32 (1986)] and pentosan polysulfate [L. Biesert et al. AIDS 2, 449 (1989)] were also studied in parallel experiments. The results of these tests are discussed below.

SUMMARY OF THE INVENTION

The present invention is directed to a method for arresting or inhibiting the growth of premalignant or malignant cells in Kaposi's Sarcoma lesions, by contacting said cells with an effective amount of SP-PG, a naturally occurring sulfated polysaccharide-peptidoglycan produced by a specific species of the bacterium Arthrobacter, AT-25. The method is effective in warm-blooded animals, including humans, and in vitro.

The invention is further directed to a method for arresting or inhibiting the growth of Kaposi's Sarcoma lesions, in warm-blooded animals including humans, by contacting cells in said lesions with an amount of the sulfated polysaccharide-peptidoglycan, SP-PG, effective to arrest or inhibit growth of said lesions.

The invention additionally provides a method for blocking or inhibiting the activity of cellular vascular permeability factor(s), which comprises contacting vascular cells with an amount of SP-PG effective to block or inhibit the activity of said factor(s). In one embodiment, the method is used to block or inhibit increased vascular permeability (and resulting edema) in diseases and disorders in which increased vascular permeability contributes to the pathology, for example, in Kaposi's Sarcoma, tumorigenesis, inflammation, diabetic retinopathy, etc.

These and other objects and advantages will become clear to one skilled in the art from a reading of the description that follows.

BRIEF DESCRIPTION OF THE DRAWINGS

FIG. 3(*a*): Control only with phosphate buffered saline (PBS);

FIG. 3(*b*): Hydrocortisone;

FIG. 3(*c*): SP-PG;

FIG. 3(*d*): SP-PG+hydrocortisone.

FIG. 4(*a*): Control only with phosphate buffered saline (PBS);

FIG. 4(*b*): Hydrocortisone;

FIG. 4(*c*): SP-PG;

FIG. 4(*d*): SP-PG+hydrocortisone.

FIG. 5(*a*): Dose response of SP-PG. Administration with (■), and without (□) tetrahydrocortisone.

FIGS. 5(*b*)–5(*e*): Inhibition of Kaposi's Sarcoma related vascular permeability by SP-PG.

FIG. 5(*b*): control phosphate buffered saline treatment;

FIG. 5(*c*): 0.5 mg SP-PG;

FIG. 5(*d*): 5 mg SP-PG;

FIG. 5(*e*): 10,000 U IFNα.

FIG. 6(*a*) shows the gross appearance and FIG. 6(*c*) shows the histological section of a Kaposi's Sarcoma lesion in a nude mouse after treatment with control phosphate buffered saline.

FIG. 6(*b*) shows the gross appearance and FIG. 6(*d*) shows the histological section of a Kaposi's Sarcoma lesion in a nude mouse after treatment with i.v. SP-PG (5 mg) and oral tetrahydrocortisone (1 mg).

DETAILED DESCRIPTION OF THE INVENTION

Figure 1A:
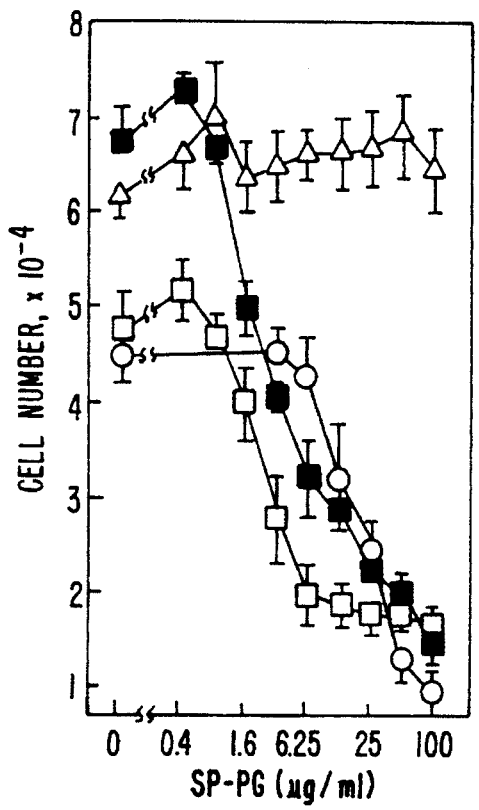
FIG. 1. The effect of SP-PG, IFNα, suramin, and pentosan polysulfate on the in vitro growth of Kaposi's Sarcoma cells, H-UVE cells, and human fibroblasts.
Figure 1B:
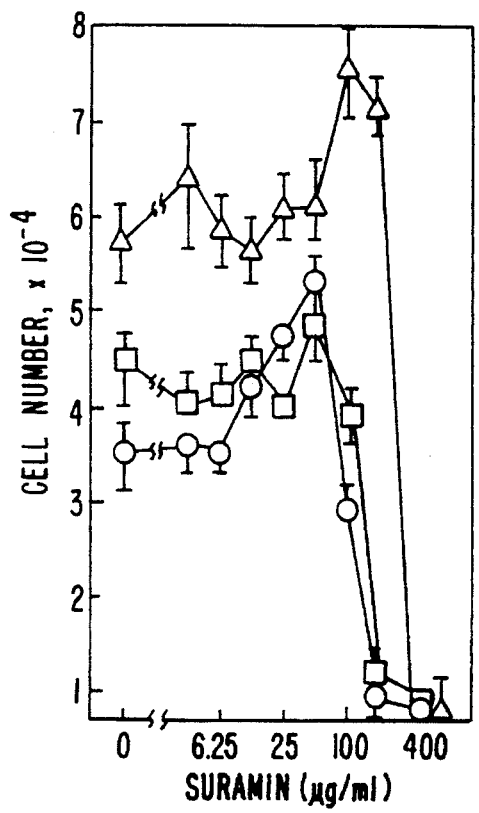
Figure 1C:
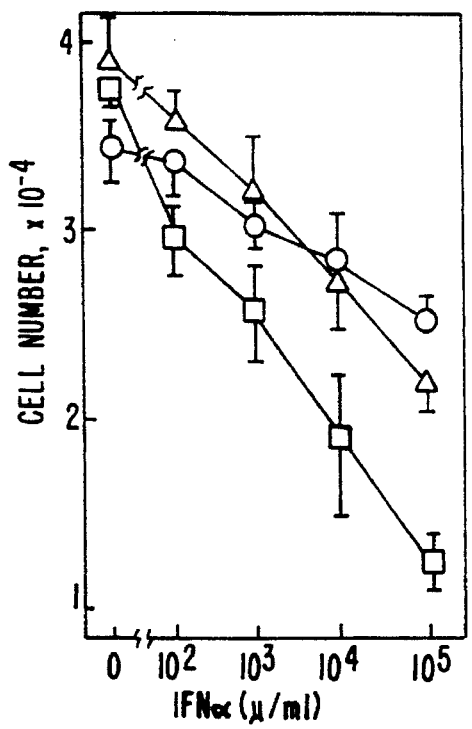
Figure 1D:
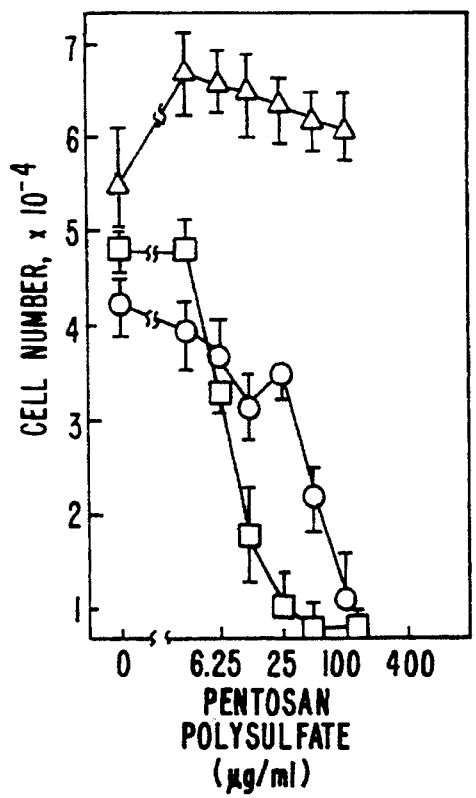

The present invention is directed to a method for blocking or inhibiting the growth of cells in Kaposi's Sarcoma lesions, by contacting the cells with an effective amount of SP-PG, a naturally occurring sulfated polysaccharide-peptidoglycan produced by a specific species of the bacterium Arthrobacter, AT-25. The method is effective in warm-blooded animals including humans and in vitro.

In another embodiment, the invention is directed to a method for arresting or inhibiting the growth of Kaposi's Sarcoma lesions, in warm-blooded animals including humans, by contacting cells in said lesions with an amount of sulfated polysaccharide-peptidoglycan SP-PG effective to arrest or inhibit growth of said lesions.

In yet another embodiment, the invention is directed to a method for preventing the appearance of Kaposi's Sarcoma lesions in warm-blooded animals including humans, by contacting vascular cells with an amount of sulfated polysaccharide-peptidoglycan SP-PG effective to prevent the appearance of said lesions.

In still another embodiment, the invention provides a method for blocking or inhibiting the activity of cellular vascular permeability factor(s), which comprises contacting vascular cells with an amount of SP-PG effective to block or inhibit the activity of said factor(s). (The term "vascular" as used herein is meant to include lymphatic vessels as well as blood vessels.) The method may be used to block or inhibit increased vascular permeability (and resulting edema) in diseases and disorders in which increased vascular permeability contributes to the pathology, for example, in Kaposi's Sarcoma, tumorigenesis, inflammation, diabetic retinopathy, etc.

SP-PG, the sulfated polysaccharide of this invention, can be obtained by removing pyrogenic substances having molecular weights of $15 \times 10^4$ or more by a suitable molecular weight fractionating method, for example, the gel filtration method, ultrafiltration method or alcohol precipitation method from DF4639 (Japanese Pat. Laid-Open No. 67301/1981) which is purified from a culture broth of the Arthrobacter species AT-25 (FERM BP-1357), which has been deposited in the name of "Micrococcus sp. AT-25" under FERM P-5255 with the Fermentation Research Institute, Agency of Industrial Science and Technology, Ministry of International Trade and Industry, the Japanese Government.

According to the gel filtration method by way of example, DF4639 is subjected to gel filtration by using a suitable carrier for gel filtration, for example, Sephacryl S-300 (trade name, product of Pharmacia AB, Uppsala, Sweden). The resulting fractions are then subjected to a high-performance gel filtration chromatography on a "G3000 SW Column" (trade name, product of Toyo Soda Mfg. Co., Ltd., Shinnanyo, Yamaguchi, Japan). Fractions (H Fraction) showing peaks in the void volume and fractions (L Fraction) giving no peaks in the void volume and eluted in a molecular weight range of about $2 \times 10^4$–$8 \times 10^4$ are separately collected and dialyzed against deionized water.

The thus-obtained inner dialyzates are separately concentrated, followed by filtration. The filtrates were separately poured with stirring into several volumes of ethanol and the resulting precipitates were separately collected. After washing the precipitate successively with 90% ethanol, ethanol and acetone, the precipitates were separately dried under reduced pressure to obtain the intended DS4152 (L Fraction) and pyrogenic substances (H Fraction).

On the other hand, the ultrafiltration can be effected by using a suitable membrane (e.g., "YM10", "YM30", "XM50" or "PM30", trade names, products of Amicon Corporation; or "NOVA 100", "OMEGA 100", "NOVA 50" or "OMEGA 50", trade names, products of Filtron Technology Corporation; or the like; typically, "YM10"), applying a pressure (0.5–5 kg/cm² or so) with nitrogen gas or by a pump and then collecting the filtrate as SP-PG. The suitable solvent may be water-ethanol (10:2–3) or water. The ultrafiltration is usually conducted at a temperature in the range of 4° C. to room temperature.

SP-PG obtained in the above manner has, as the sodium salt thereof, the following physicochemical characteristics:

(1) Molecular weight (by the gel filtration method):

29,000±3,000

(2) Elemental analysis (ranges of 5 lots):

C:24.42–25.76%

H:3.34–3.98%

N:0.51–0.89%

S:10.6–11.7%

P:0.77–1.06%

(3) Sugar and protein contents:

Sugar content (%): 57±3 (by the phenol-sulfuric acid method; standard: galactose)

Protein content (%): 1±0.5 (by the Lowry-Folin's method; standard: bovine serum albumin)

(4) Specific rotatory power:

$[\alpha]_D{}^{25}$:$-37°\pm1°$ (0.5% aq. solution)

(5) Characteristic absorption bands in infrared absorption spectrum:

1240, 840 (shoulder), 810 (cm$^{-1}$ KBr)

(6) Solubility:

Freely soluble in water but practically insoluble in organic solvents such as ether, benzene, chloroform, methanol and ethanol.

(7) Color reaction:

Positive in the phenol-sulfuric acid reaction, anthronesulfuric acid reaction, biuret reaction and Lowry-Folin's reaction. In the form of an acid hydrolyzate, also positive in the Elson-Morgan's reaction and ninhydrin reaction. Negative in the carbazole reaction and Sakaguchi reaction.

(8) Distinction of acidic, neutral or basic:

pH 6–8 (3% aqueous solution)

(9) Contents of constituent sugar, sulfate groups and phosphorus:

The molar ratio of D-glucose:D-galactose:$SO_3{}^-$:Na:P-(phosphorus) is approximately 10:61:73:6.

(10) Constituent amino acids and amino sugars:

An analysis of an acid hydrolysate by an amino acid analyzer indicates the existence of alanine, glycine, glutamic acid, diaminopimelic acid, glucosamine and muramic acid.

As discussed above, the diseases in which increased vascular permeability contributes to the disease pathology and in which the administration of SP-PG is beneficial include, for example, Kaposi's Sarcoma, tumorigenesis, inflammation, and diabetic retinopathy and edema.

Although the above-described SP-PG itself blocks or inhibits the activity of cellular vascular permeability factors, these effects are enhanced when SP-PG is combined with any anti-edema agent.

(1) For example, SP-PG may be combined with cortisone and its derivatives (acetate, enanthate, undecylate, etc.); hydrocortisone and its derivatives (acetate, hemisuccinate, caproate, etc.); prednisone and its derivatives; prednisolone and its derivatives (acetate, hemisuccinate, phosphate, butylacetate, tetrahydrophthalate, trimethylacetate, etc.); methylprednisolone and its derivatives (acetate, hemisuccinate, etc.); and betamethasone and its derivatives (phosphate, valerate, etc.).

Certain glucocorticoid isomers in which the 11-hydroxyl group has the α-configuration, for example, 11α-epihydrocortisone; and tetrahydrometabolites of the above-mentioned glucocorticoids, irrespective of glucocorticoid activity.

Corpus luteum hormones progesterone and hydroxyprogesterone, and their derivatives (acetates, etc.); dydrogestrone and its 17α-acetoxy derivative (Duphaston, trade name); etc. In addition, the effects of SO4P-PG are enhanced when it is combined with mineralocorticoids, aldosterone and desoxycorticosterone, and their derivatives (acetates, trimethylacetates, enanthates, phenylpropionates, etc.).

(2) Steroid hormones containing the androstane nucleus, namely, androgens:

Androsterone and testosterone, and their derivatives (propionates, enanthates, butyrates, caprylate, etc.).

Epithiostanol and mepitiostanon, and their derivatives.

Fluoxymesterone and its derivatives; methyltestosterone and its derivatives; and stanolone and its derivatives.

(3) Steroid hormones containing the estrane nucleus, namely, follicle hormones:

Estrone and its derivatives; estradiol and its derivatives (benzoate, dipropionate, valerate, undecenoate, etc.); estriol and its derivatives (tripropionate, etc.).

As exemplary antiestrogens on the other hand, may be mentioned clomiphene, nafoxidine, tamoxifen, 4-hydroxytamoxifen and N-desmethyltamoxifen, and physiologically-acceptable salts thereof, e.g., their organic acid salts such as citrate, their inorganic acid salts such as hydrochloride, etc.

Thus, the pharmaceutical formulation of the present invention may comprise a pharmaceutically acceptable carrier, and as the active ingredient, SP-GP, either alone or in combination with cortisone or a derivative of cortisone. The active ingredient is present in the formulation in an amount sufficient to block or inhibit the activity of cellular vascular permeability factors.

The pharmaceutical formulation may be in the form of a solution, powder, granule, tablet, injection, or suppository.

The formulation may be administered intravenously, intra-arterially, orally, subcutaneously, intrarectally, mucosally or directly into the affected tissue or lesion.

Appropriate individual dosages can be readily determined by one skilled in the art. The frequency of administration and the amount administered to effect treatment depends on the mode of administration of the active ingredient, the needs of the particular patient, the particular disease, etc., and can readily be determined by one skilled in the art.

In vitro experiments have demonstrated that SP-PG showed some specificity in that it affected the growth of Kaposi's Sarcoma cells and at higher concentrations also the growth of normal vascular endothelial cells (H-UVE) but not fibroblasts when incubated with or without growth factors suitable for each cell type. As illustrated in FIG. 1, the Kaposi's Sarcoma spindle cells were more sensitive than the normal endothelial cells. $IC_{50}$ (concentration at which 50% inhibition was obtained) was 3 µg/ml for Kaposi's Sarcoma cells and 25 µg/ml for H-UVE cells. Fibroblasts, however, remained unaffected at all concentrations tested. Hydrocortisone, previously found to augment the growth of Kaposi's Sarcoma cells in the presence of activated T cell conditioned medium, increased the $IC_{50}$ of SP-PG on Kaposi's Sarcoma cells to 12.5 µg/ml (FIG. 1). In contrast, hydrocortisone inhibited the growth of H-UVE cells more effectively than SP-PG alone, while growth of fibroblasts was not affected by a combination of SP-PG and hydrocortisone as it was not affected by SP-PG alone.

Pentosan polysulfate also inhibited the in vitro growth of Kaposi's Sarcoma and H-UVE cells, but only at higher concentrations ($IC_{50}$ for Kaposi's Sarcoma cells was 12.5 µg/ml and that for H-UVE cells 50 µg/ml). Neither suramin ($IC_{50}$, 100 µg/ml) nor IFNα ($IC_{50}$ 10,000 U/ml).appreciably affected Kaposi's Sarcoma or H-UVE cell growth (FIG. 1).

Figure 2:
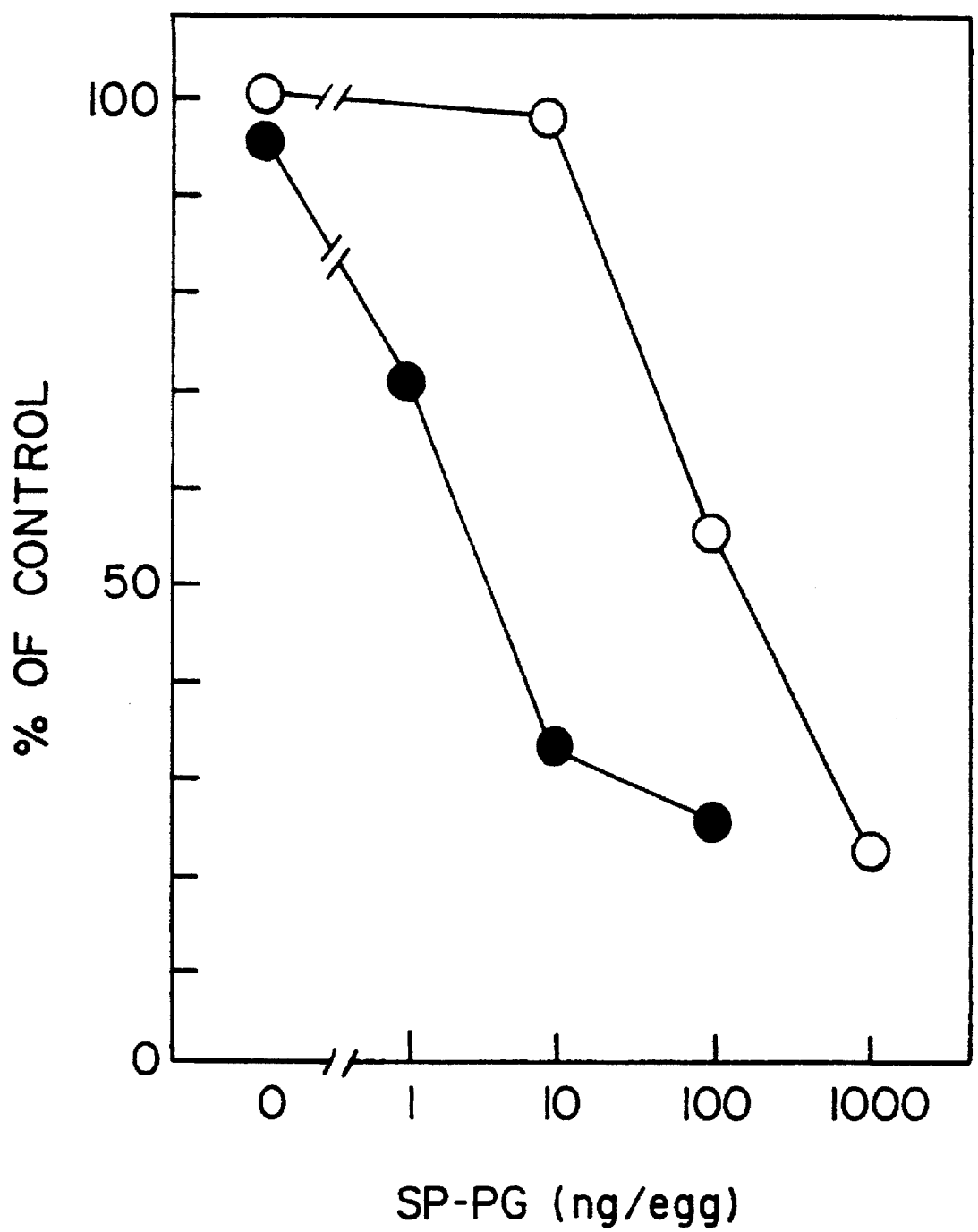
FIG. 2. The inhibition of normal chick embryonic angiogenesis by SP-PG alone and in combination with tetrahydrocortisone.
Figure 3A:
FIG. 3. The inhibition of angiogenesis induced by Kaposi's Sarcoma cells on chick chorioallantoic membranes by SP-PG. Under low magnification in a biocular microscope, halo-like angiogenesis of the peripheral regions is observed.
Figure 3B:
Figure 3C:
Figure 3D:
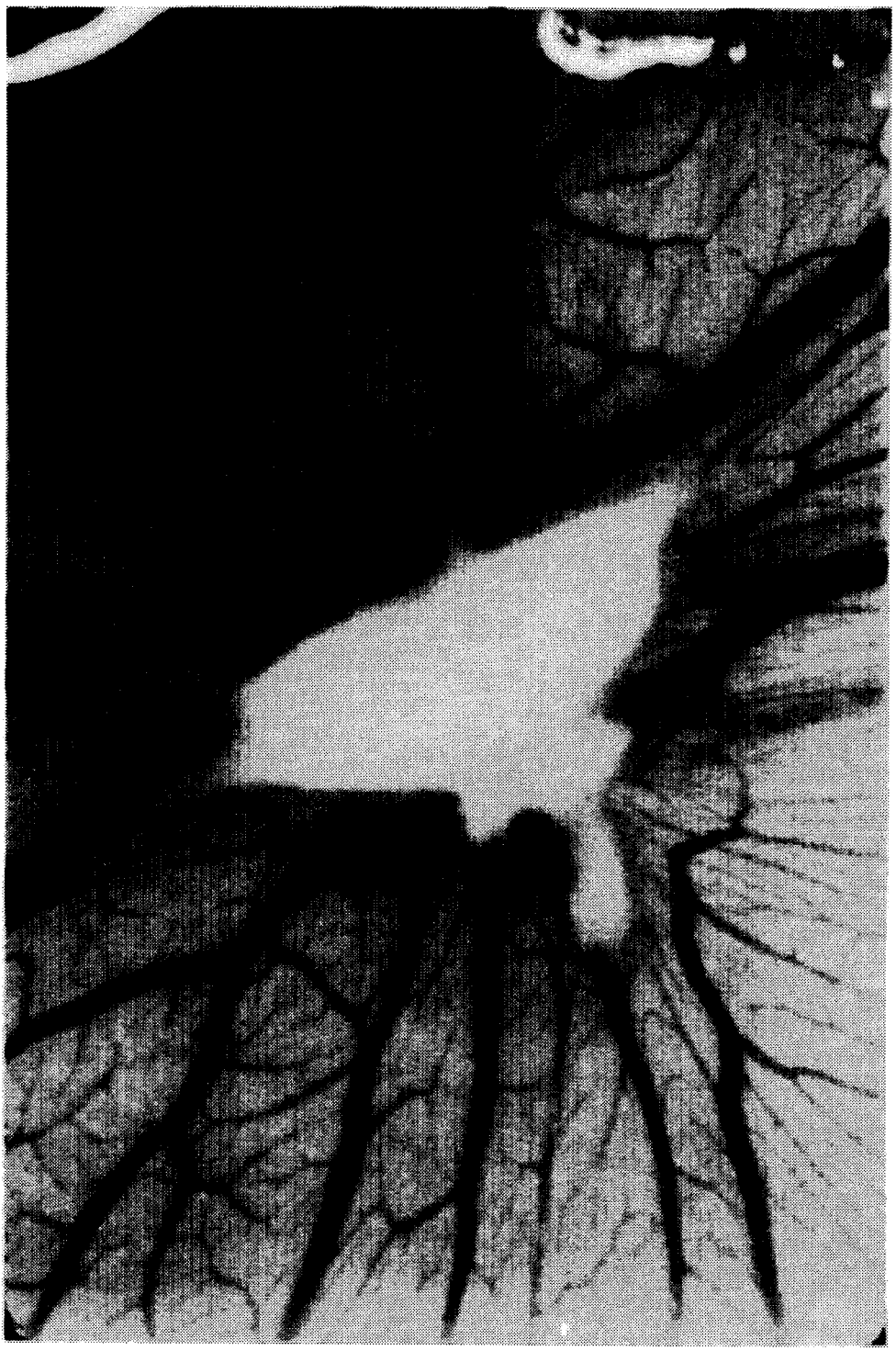
Figure 4A:
FIG. 4. The inhibition of angiogenesis induced by Kaposi's Sarcoma cells on chick chorioallantoic membranes by SP-PG. The CAM is fixed with 4% paraformaldehyde and stained with giemsa.
Figure 4B:
Figure 4C:
Figure 4D:
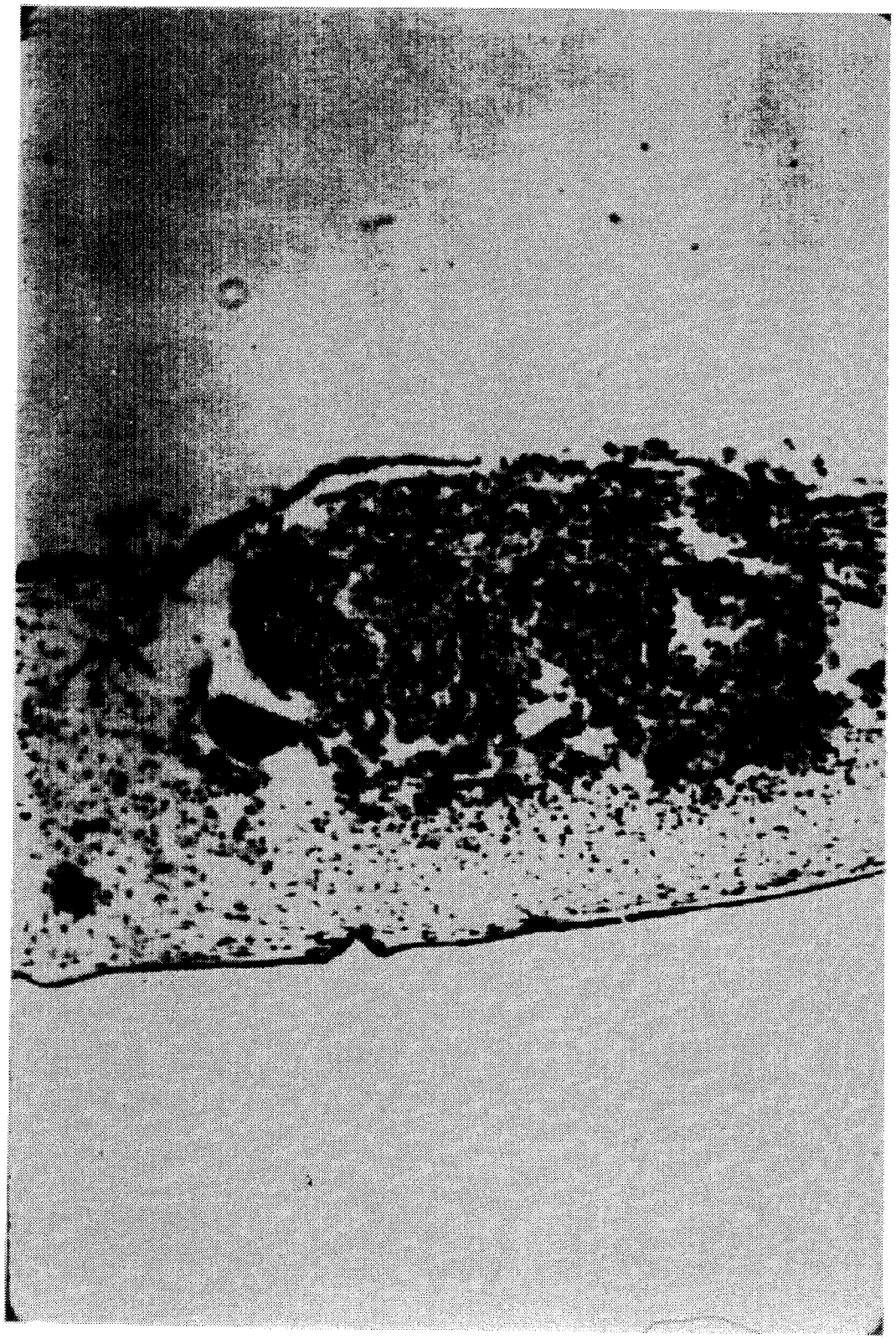

CAM assays were used to evaluate the effect of SP-PG on new blood vessel formation. As previously reported [(N. Tanaka et al., Cancer Res. 49, 6726 (1989)] and as shown in FIG. 2, new vessel formation was suppressed by addition of SP-PG. Unexpectedly, the effect of SP-PG was augmented by the addition of tetrahydrocortisone (FIG. 2). Also, the formation of halo-like angiogenic lesions [S. Z. Salahuddin et al. Science 242, 430 (1988)], induced by Kaposi's Sarcoma cells ($1 \times 10^5$), which normally reach 1–1.5 cm in diameter (FIG. 3), was inhibited by treatment with SP-PG. When 25 µg of SP-PG was added to the lesion once a day for 4 days, i.e., the angiogenic lesion diminished to less than 0.5 cm. Higher concentrations (100 µg) produced more dramatic suppression of growth so that the only evidence of visible angiogenesis was in close proximity to the Kaposi's Sarcoma cells themselves. A summary of the effects of SP-PG on Kaposi's Sarcoma cell angiogenesis in CAM assay is set forth in Table 1 below.

TABLE 1

A Summary of the Effects of SP-PG on Kaposi's Sarcoma Cell Angiogenesis in CAM Assay

| Compounds (µg) | Angiogenesis | | Numbers of CAM Assays |
|---|---|---|---|
| | Peripheral Lesion | Central Lesion | |
| Phosphate buffered saline SP-PG | 1–1.5 cm halo-like angiogenesis | Angiogenesis and edema in lesion | 16 |
| 25 | Angiogenesis diminished (under 0.5 cm) | Angiogenesis and edema remained | 6 |
| 100 | Angiogenesis regressed and remained very near KS* cells | Angiogenesis and edema partially inhibited | 4 |
| 25 + hydrocortisone | Complete inhibition of angiogenesis | Angiogenesis and edema strongly inhibited | 4 |

*KS - Kaposi's Sarcoma

Similar to the in vivo effects on angiogenesis in the CAM assays but in contrast to the in vitro effects on cell growth, a synergistic effect was observed when a combination of SP-PG (25 µg) and hydrocortisone (20 µg) was used in this assay (FIGS. 3 and 4).

As described previously, nude mice can be used to study at least two biological properties of Kaposi's Sarcoma-like lesion development, i.e., increased vascular permeability and angiogenesis. (Both edema and new blood vessel formation are hallmarks of the Kaposi's Sarcoma tumor.) When $2-4 \times 10^6$ Kaposi's Sarcoma-3 cells are subcutaneously injected into the backs of the nude mice, or administered intraperitoneally (i.p.), a biphasic vascular permeability response is observed. The first is a nonspecific early, histamine dependent phase occurring approximately 30 minutes postinoculation and the second, an Kaposi's Sarcoma cell-induced late, prolonged and histamine-independent phase, occurring approximately 12 hours post-inoculation. In addition, angiogenesis is induced in these subcutaneous lesions and the growth of spindle-shaped cells of murine origin is observed 5 to 6 days after transplantation of the human cultured Kaposi's Sarcoma cells [S. Z. Salahuddin et al. Science 242, 430 (1988)]. These in vivo systems were used to study the effect of SP-PG and other agents on the development of the Kaposi's Sarcoma lesion.

Figure 5A:
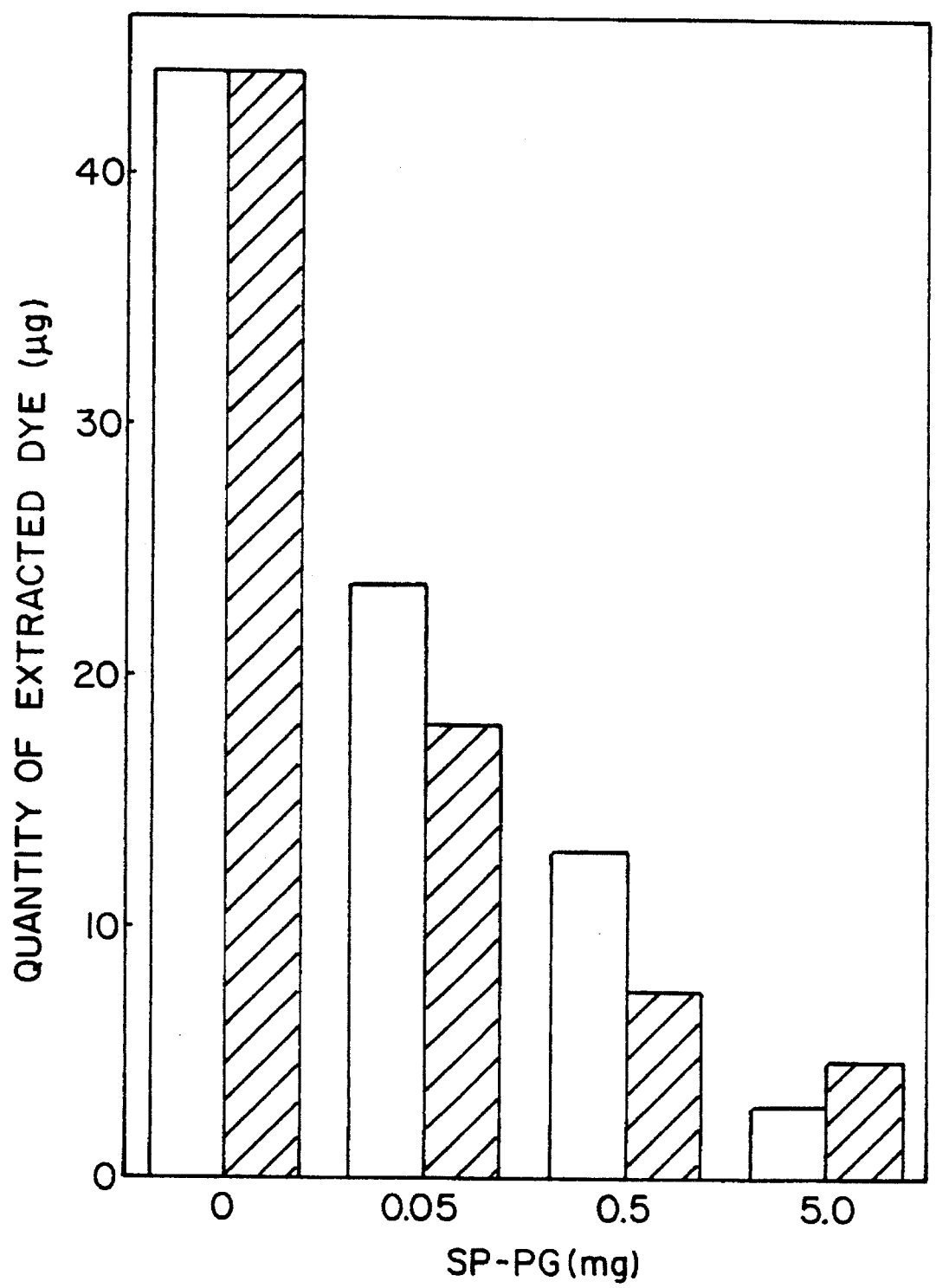
FIG. 5. The effect of different concentrations of SP-PG and of IFNα on the vascular permeability response induced by Kaposi's Sarcoma cells.
Figure 5B:
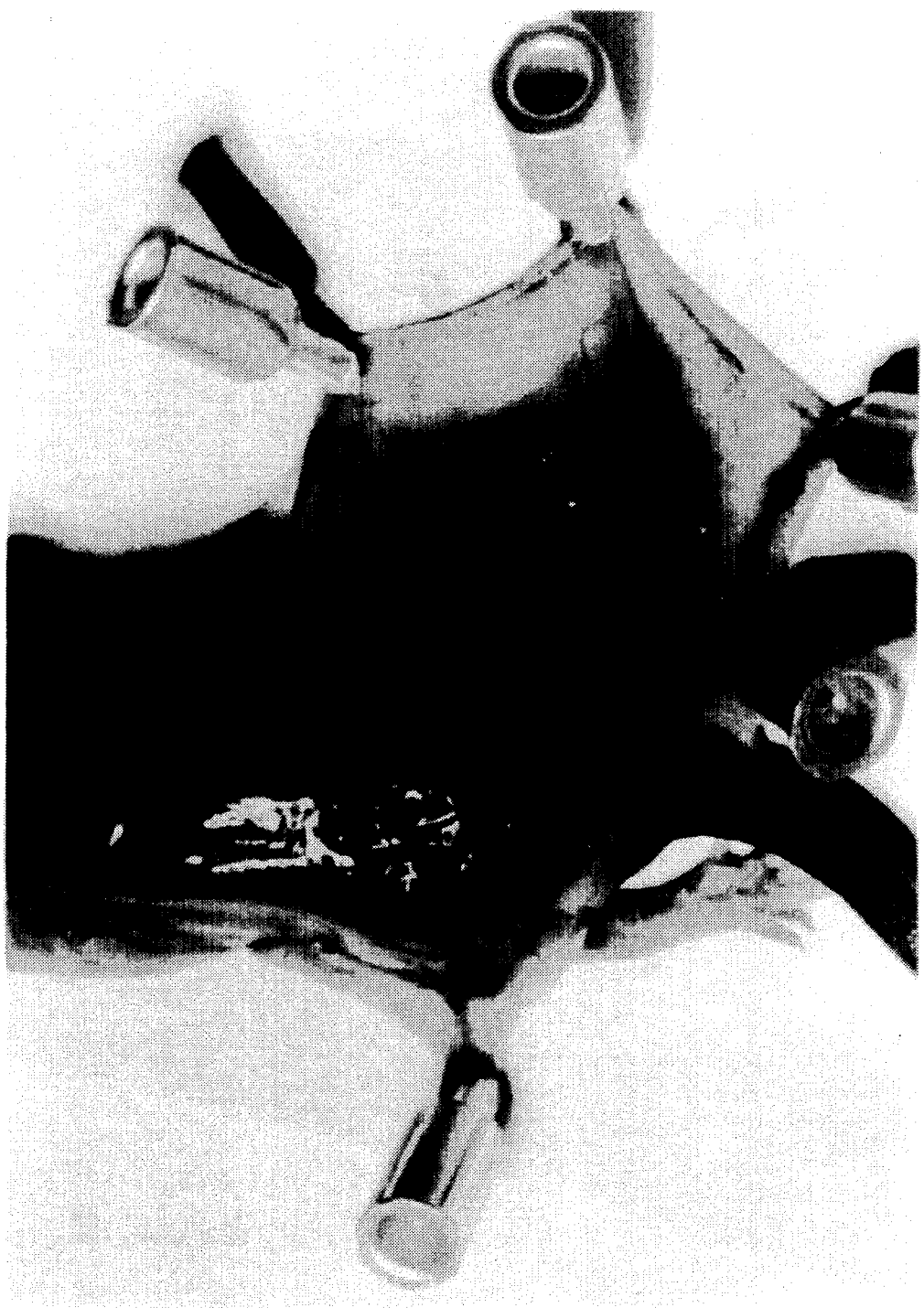
Figure 5C:
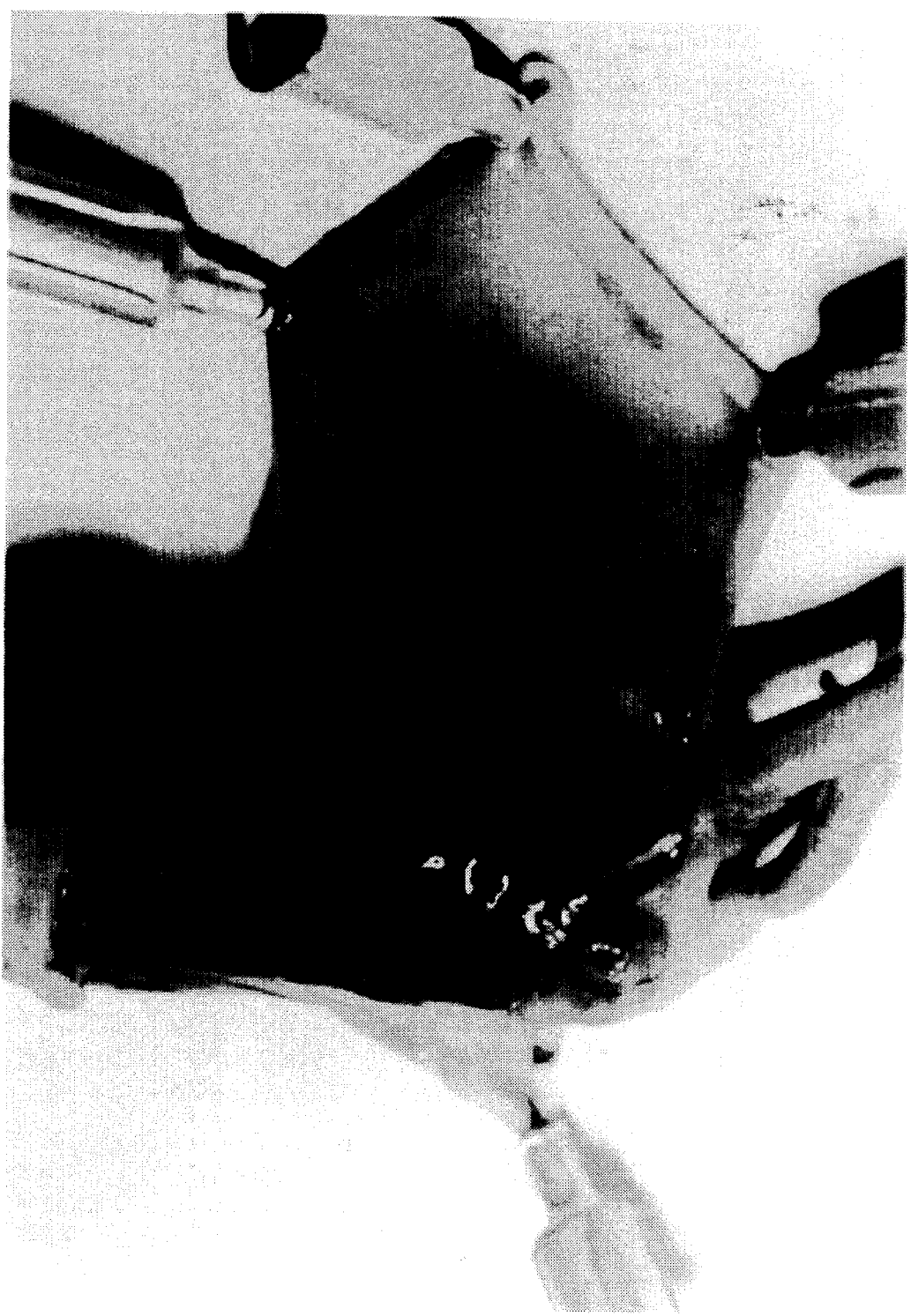
Figure 5D:
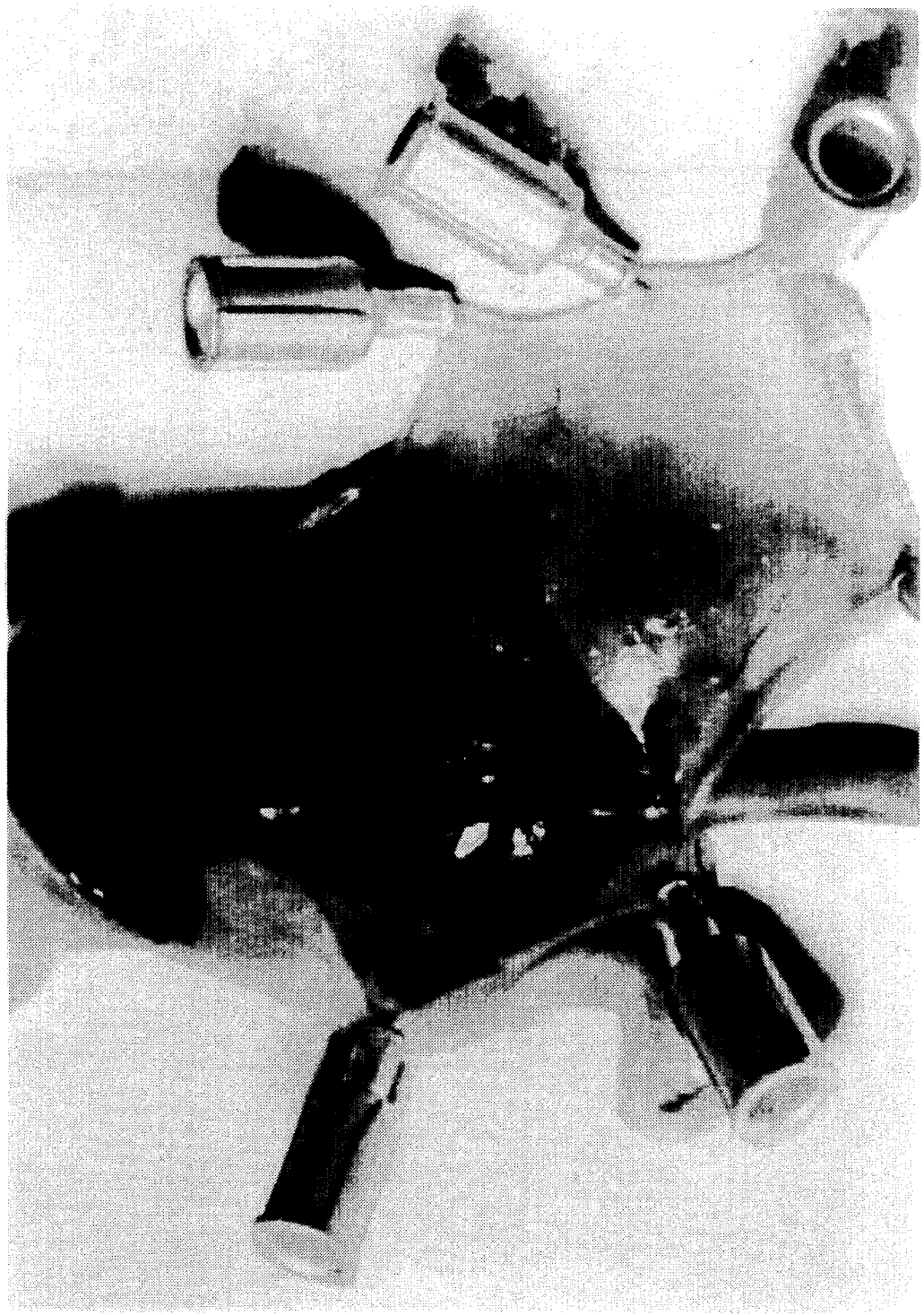
Figure 5E:

Mice, subcutaneously inoculated with Kaposi's Sarcoma cells, were intravenously (i.v.) or i.p. administered either SP-PG, IFNα, suramin, or pentosan polysulfate. As indicated in FIGS. 5(a) through 5(d), SP-PG inhibited the induction of the late vascular hyperpermeability phase induced by Kaposi's Sarcoma cells in a dose dependent manner beginning at a dose as low as 0.5 mg (25 mg/kg). Oral administration of tetrahydrocortisone in peanut oil did not significantly affect this response. In contrast, the non-specific, early, histamine-dependent, phase of hyperpermeability was not affected by SP-PG. A high dose of IFNα (10,000 U i.v.) ($5 \times 10^5$ U/kg) also partially inhibited the late phase response [FIG. 5(e)]. Even high concentrations of suramin (5 mg i.p.) (250 mg/kg) or pentosan polysulfate (2 mg i.v.) (100 mg/kg) had no effect with or without the addition of tetrahydrocortisone. A comparison of the relative effects of SP-PG and various other agents on the increase in vascular permeability induced by Kaposi's Sarcoma cells is shown in Table 2 below.

TABLE 2

Comparison of the Relative Effects of SP-PG and Various Other Agents on the Increase in Vascular Permeability Induced by Kaposi's Sarcoma Cells

| Compound | Dose/Mouse | No. of Mice | Injection Site | Injection Interval | Inhibition of Increased Vascular Permeability* |
|---|---|---|---|---|---|
| SP-PG | 0.05 mg | 10 | i.v. | Time 0 | + |
|  | 0.5 mg | 10 |  |  | ++ |
|  | 5.0 mg | 18 |  |  | +++ |
| IFNα | 10,000 U | 5 | i.v. | Time 0 | ++ |
| Suramin | 5.0 mg | 5 | i.p. | Time 0 and 6 hr | 0–± |
| Pentosan polysulfate | 2.0 mg | 5 | i.v. | Time 0 and 6 hr | 0–± |

*Vascular permeability was induced by subcutaneous injection of $4 \times 10^6$ cells into athymic nude mice and measured by Evans blue dye as described in the body of the Detailed Description of the Invention and Example 4.
0 = No inhibition
± = Very slight inhibition (barely detectable)
+, ++, +++ = range of significant inhibition (+++, inhibition complete)

In order to evaluate the effect of SP-PG on Kaposi's Sarcoma cell induced angiogenesis, nude mice were inoculated intravenously with 0.05 (2.5 mg/kg), 0.5 (25 mg/kg), or 5 mg (250 mg/kg) SP-PG with or without oral administration of 1 mg tetrahydrocortisone given once a day for 5 days. While 0.05 mg of SP-PG did not affect angiogenesis even in combination with tetrahydrocortisone, 0.5 mg of SP-PG led to some degree of degeneration of newly formed vascular lesions and 5 mg of SP-PG completely inhibited vascularization. Unlike vascular permeability, the effect on angiogenesis was even more pronounced when 5 mg SP-PG was combined with 1 mg tetrahydrocortisone (FIG. 6). All mice remained healthy and active. Histological examination of the lesions in the nude mice demonstrated degenerated vascular structures and fewer blood vessels, less bleeding, and only a few spindle shaped cells, compared to untreated control animals (FIG. 6). In similar experiments, 5 mg of suramin was found to be toxic, i.e., 2 of 5 nude mice died during experiments and the remaining mice showed evidence of lethargy and weakness. IFNα (10,000 U) had only a limited effect and 2 mg pentosan polysulfate had no inhibitory effect on the development of these angiogenic lesions (Table 3).

A comparison of the relative effects of SP-PG and various other agents on angiogenesis induced by Kaposi's Sarcoma cells is shown in Table 3 below.

TABLE 3

Comparison of the Relative Effects of SP-PG and Various Other Agents on Angiogenesis Induced by Karposi's Sarcoma Cells

| Compound | Dose/Mouse* | No. of Mice | Injection Site | Inhibition of Angiogenesis+ |
|---|---|---|---|---|
| SP-PG | 0.05 mg | 10 | i.v. | 0–± |
|  | 0.5 mg | 10 |  | ++ |
|  | 5.0 mg | 18 |  | +++ ‡ |
| IFNα | 10,000 U | 5 | i.v. | + |
| Suramin | 5.0 mg | 5 | i.p. | +++ |
| Pentosan polysulfate | 2.0 mg | 5 | i.v. | 0–± |

*All animals were treated daily for 6 days
‡Angiogenesis was induced by subcutaneous injection of $4 \times 10^6$ cells into athymic nude mice. Angiogenic lesions, observed at day 6 were fixed and stained for evaluation as described in the body of the Detailed Description of the Invention and in Example 6.
Since suramin produced serious lethargy and weakness in nude mice, this inhibition might be related to a toxic, non-specific effect. Changes in the KS-like lesion after suramin was slight and readily distinguished from the much greater effects of SP-PG.
0 = No inhibition
± = Very slight inhibition (barely detectable)
+, ++, +++ = Range of significant inhibition (+++, inhibition complete)

Recent observations suggest that Kaposi's Sarcoma may be a factor-mediated disease where cytokines, hormones and/or other biological agents play important roles in the development, maintenance and spread of typical lesions [S. Nakamura et al. Science 242, 426 (1988); S. Z. Salahuddin et al. Science 242, 430 (1988); B. Ensoli et al. Science 243, 223 (1989); and reviewed in R. C. Gallo Quatrieme Colloque Des Cent Gardes (Proceedings, Biomedical Research Strategy on AIDS) 113 (1989) and B. Ensoli et al. Hematol. Oncol. Clin. North Am. 5, 281 (1991)]. The long-term culture systems for the growth of Kaposi's Sarcoma-derived spindle shaped cells and the previously developed in vivo models can be used to assess the efficiency of potential therapeutic agents on some of the important histological features of Kaposi's Sarcoma lesion development, such as angiogenesis, edema and growth of spindle shaped cells. These assay systems could, therefore, provide an opportunity to develop strategies for the management of Kaposi's Sarcoma.

A number of older known inhibitors of angiogenesis, such as protamine sulfate [S. Taylor and S. Folkman Nature 297, 307 (1982)] and heparin or heparin analogs [S. Taylor and S. Folkman Nature 297, 307 (1982); J. Folkman et al. Science 243, 1490 (1989)] with angiostatic steroids [J. Folkman and D. E. Ingber Ann. Surg. 206, 374 (1987)] have been tested on CAM or tumor-associated angiogenic systems. However, these compounds have shown significant toxicity or induced bleeding. Recently, other angiostatic agents have also been described such as platelet factor 4 [T. E. Maione et al. Science 247, 77 (1990)], cartilage-derived inhibitor [M. A. Moses et al. Science 248, 1408 (1990)] and a fungus product or its analog [D. Ingber et al. Nature 348, 555 (1990)]. The present inventors have not yet tested these in their Kaposi's Sarcoma model systems. Instead, the inventors chose to compare agents already in clinical use in Kaposi's Sarcoma and to compare their effects with SP-PG, selected because of its apparent lack of in vitro cytotoxicity. In the present study, SP-PG was found to be particularly promising for Kaposi's Sarcoma because of its low cytotoxicity and by its efficiency in limiting Kaposi's Sarcoma cell growth and Kaposi's Sarcoma-like lesion development. This is consistent with a previous report [N. Tanaka et al. Cancer Res. 49, 6726 (1989)] in which SP-PG was found to inhibit spontaneous embryonic CAM angiogenesis and tumor-induced angiogenesis, in which repeated subcutaneous administration resulted in the prolonged survival of mice injected with solid tumor cells [No Tanaka et al. *Cancer Res.* 49, 6726 (1989)], though these past studies did not include Kaposi's Sarcoma.

The mechanism of its effect in inhibition of Kaposi's Sarcoma is believed to be due to its inhibition of spindle cell growth shown in these studies. Although the molecular mechanism of this effect is not understood, since it is a sulfated compound it is believed to function by a mechanism similar to that suggested for heparin or heparin analogs, i.e., as a heparinoid [S. Taylor and S. Folkman *Nature* 297, 307 (1982); J. Folkman et al. *Science* 243, 1490 (1989); J. Folkman and D. E. Ingber *Ann. Surg.* 206, 374 (1987)].

In the inventors' in vitro and in vivo systems, two important components of Kaposi's Sarcoma lesion development, i.e., vascular hyperpermeability and angiogenesis, can be independently evaluated. Since vascular hyperpermeability (an efficient way for developing lesions to receive needed cellular as well as extracellular materials), vascular proliferation, and other vascular responses are involved in a variety of pathological situations, such as tumorigenesis, inflammation, and diabetic retinopathy, the development of methods to prevent or reverse their effects is expected to have broad implications for disease treatment. A better understanding of the effect of such potential therapeutic agents in these systems is also expected to yield important insights into physiological as well as pathological processes, i.e., on development of edema, inflammation, and tumor cell growth as well as their management. Thus, these systems are expected to prove useful both for the evaluation of candidate drugs for possible effectiveness against a variety of vascular proliferative disorders as well as for helping to gain information on basic biological processes. In this regard SP-PG is expected to be a candidate for therapy not only of Kaposi's Sarcoma but for these other disorders, as well as being a useful tool for basic studies of these phenomena.

The present invention will be illustrated in detail in the following examples. These examples are included for illustrative purposes only and should not be considered to limit the present invention.

EXAMPLE 1

Effect of SP-PG, IFNα, Suramin, and Pentosanolysulfate on the in Vitro Growth of Kaposi's Sarcoma Cells, H-UVE Cells, and Human Fibroblasts Kaposi's Sarcoma-3 cells ($3\times10^3$) established in the NCI laboratory [P. A. Volberding et al. *Ann. Intern. Med.* 103, 335 (1985)] were cultured in RPMI 1640 medium supplemented with 15% fetal calf serum (FCS) (Inovar, Gaithersburg, MD), 12.5% activated CD4 positive T cell-derived conditioned medium (T-cell CM) (□) or T cell CM with $10^{-6}$ M hydrocortisone (■) in 0.5 ml (Hydrocorton, Merck, Sharp and Dhome, West Point, Pa.). Human umbilical vein endothelial cells (H-UVE) ($5\times10^3$) established in the NCI laboratory [P. A. Volberding et al. *Ann. Intern. Med.* 103, 335 (1985)] were cultured in RPMI 1640 medium supplemented with 15% FCS, 30 µg/ml endothelial cell growth supplement (Collaborative Research, Lexington, Mass.) with 45 µg/ml heparin (o) (Sigma, St. Louis, Mo.). These cells in 0.5 ml media were plated in gelatinized 24 well tissue culture dishes. Human skin fibroblasts (HSF), the gift from Dr. Stuart Aaronson at the National Institutes of Health, ($3\times10^3$) were cultured in Dulbecco's modified Eagle's medium (DMEM) (ABI, Silver Spring, Md.) supplemented with 10% FCS (Δ). Cells were plated in ungelatinized tissue culture dishes in 0.5 ml. These cultures were incubated with or without 0.4–100 µg/ml SP-PG (Daiichi Pharmaceutical Co., Ltd., Tokyo, Japan), 1.6–400 µg/ml suramin (FBA Pharmaceutical Division, Mobay Chemical Corporation, New York, N.Y.), $10^2$14 $10^5$ U/ml human recombinant interferon α ($3\times10^8$ U/mg), kindly provided by Dr. Rashidbaigi at the University of Medicine and Dentistry of N.J.) and 3–100 µg/ml pentosan polysulfate (Bering Werke, Germany) (provided by Dr. Browning at the Laboratory of Tumor Cell Biology), respectively. Compounds and medium were replaced every 2 days for H-UVE cells and every 3 days for Kaposi's Sarcoma cells and fibroblasts. Cells at day 6 of culture were trypsinized and counted by Coulter particle counter [P. A. Volberding et al. *Ann. Intern. Med.* 103, 335 (1985)].

The effect of SP-PG, IFNα, suramin, and pentosanolysulfate on the in vitro growth of Kaposi's Sarcoma cells, H-UVE cells, and human fibroblasts are shown in FIG. 1.

EXAMPLE 2

Inhibition of Normal Chick Embryonic Angiogenesis by SP-PG Alone and in Combination with Tetrahydrocortisone To examine the direct activity of SP-PG (o) or SP-PG + tetrahydrocortisone (0.1 ng/egg, ●), a mixture of 5 µl of saline solution containing test material and 5 µl of 1% (w/v) saline solution of methyl cellulose was added to the 5 day chorioallantoic membrane (CAM) of fertilized Norin Cross chicken eggs (Funahashi Farm, Funahashi, Japan). After 2 days, embryonic angiogenesis of the treated group was compared with that of the control. The doses required to inhibit 50% of embryonic vascularization ($IDa_{50}$ values) were calculated by probit analysis on the basis of T/C%.

The inhibition of normal chick embryonic angiogenesis by SP-PG alone and in combination with tetrahydrocortisone is shown in FIG. 2.

EXAMPLE 3

Angiogenesis Induced by Kaposi's Sarcoma Cells on Chick Chorioallantoic Membranes Inhibited by SP-PG Fertilized eggs were cracked and embryos were transferred into 10 cm culture dishes and incubated at 37° C., in a $CO_2$ incubator with 70% humidity on the first day. On day 9 the chorioallantoic membranes of well developed embryos were selected for angiogenesis experiments. One x $10^5$ KS-3 cells were placed on the CAM and new blood vessel formation was observed for the next 4 days. SP-PG, hydrocortisone, or SP-PG+hydrocortisone in 30 µl were dropped on the lesion daily for 4 days.

The inhibition of angiogenesis induced by Kaposi's Sarcoma cells on chick chorioallantoic membranes by SP-PG is shown in FIGS. 3 and 4. Halo-like angiogenesis of the peripheral regions was observed under low magnification in a biocular microscope as shown in FIG. 3, and the CAM was fixed with 4% paraformaldehyde and stained with giemsa in FIG. 4. The response in the center of the lesion was evaluated by histologic examination and is summarized in Table 1.

EXAMPLE 4

Effect of Different Concentrations of SP-PG and of IFNα on the Vascular Permeability Response Induced by Kaposi's Sarcoma Cells Eight week old female Balb/c nu/nu athymic nude mice were supplied by Frederick NIH Cancer Research Facility and used during all experiments (20 g body weight). After the mice were treated with various compounds (control phosphate buffered saline treatment; 0.5 mg SP-PG; 5 mg SP-PG; and 10,000 U IFNα) with or without initial peroral administration of 1 mg tetrahydrocortisone in peanut oil (Sigma), $2\times10^6$ Kaposi's Sarcoma-3 cells were injected subcutaneously. The resulting late phase vascular permeability response was observed 12 hours after injection. At that time 100 µl of 5 mg/ml Evans blue (Sigma) was injected into the tail vein and 15 minutes later dye which had exuded into the extracellular space was extracted and measured by a spectrophotometer [FIG. 5(a)] and the appearance of the tissue recorded photographically [FIG. 5(b)]. The effect of different concentrations of SP-PG and of IFNα on the vascular permeability response induced by Kaposi's Sarcoma cells is shown in FIGS. 5(a) through 5(e).

EXAMPLE 5

SP-PG Induced Regression of Kaposi's Sarcoma-Like Lesions in Nude Mice

Figure 6A:
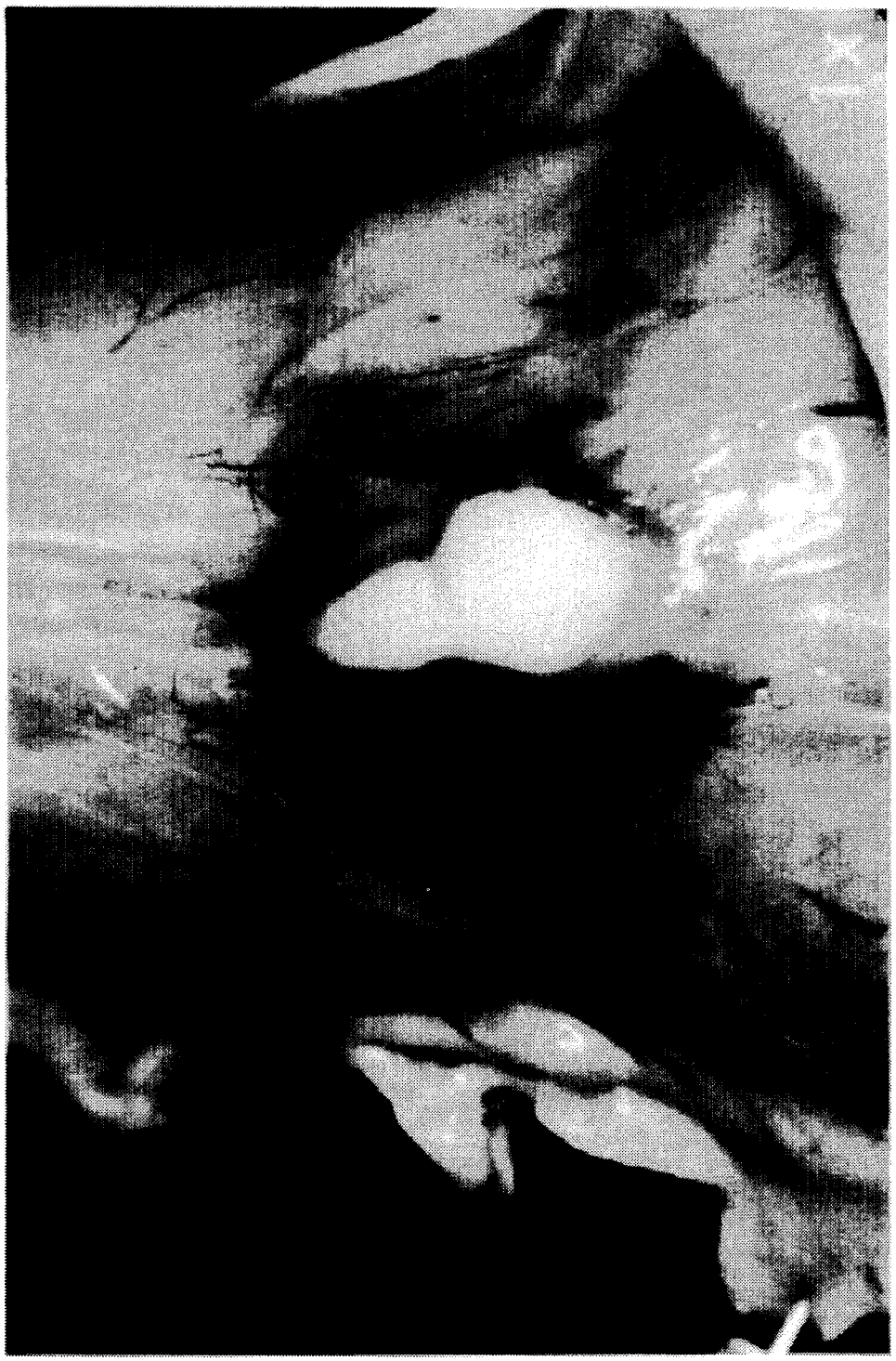
FIG. 6. SP-PG induced regression of Kaposi's Sarcoma-like lesions in nude mice. (>) Represents the spindle shaped cells and (↑) the small vessels.
Figure 6B:
Figure 6C:
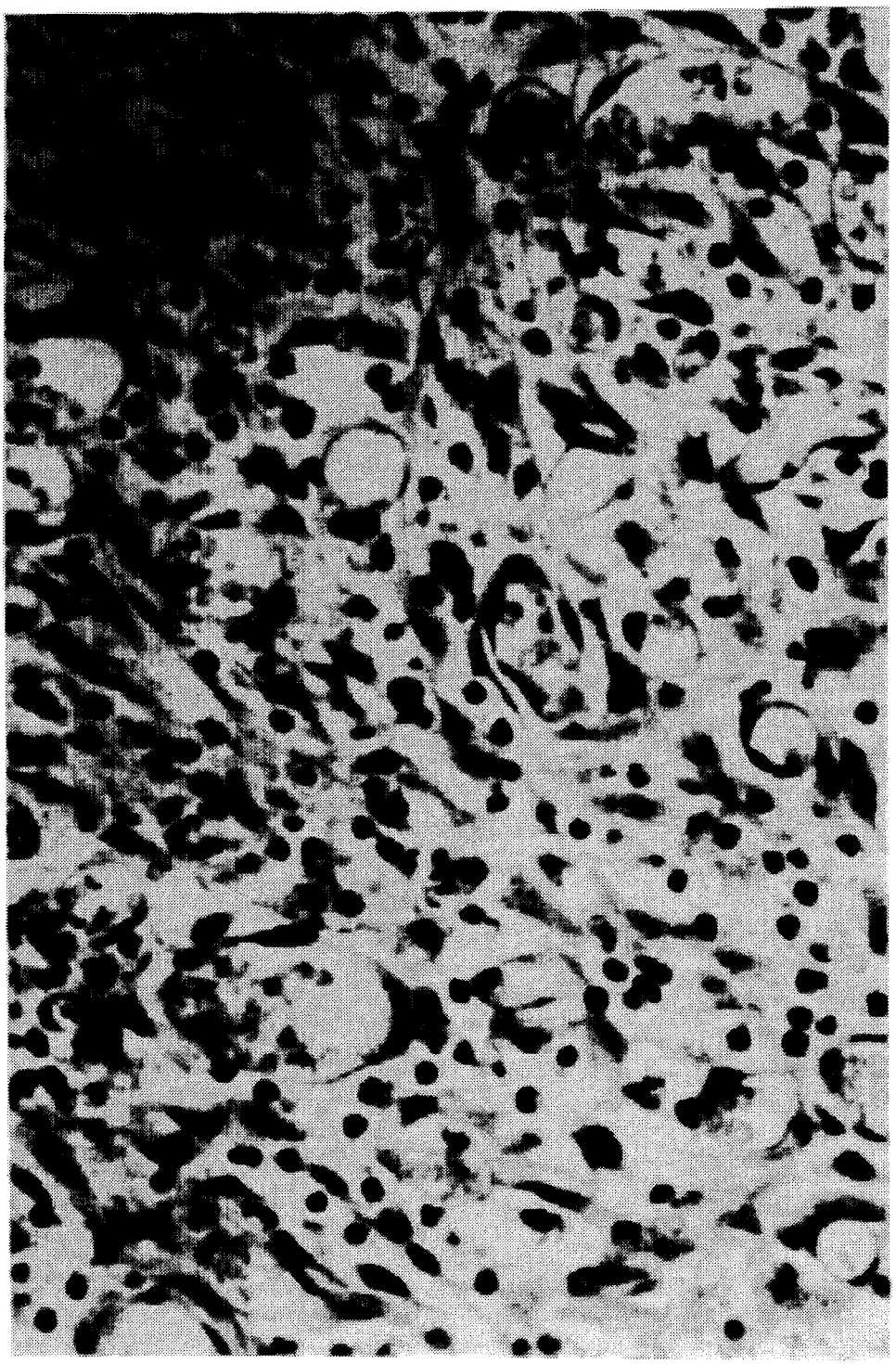
Figure 6D:
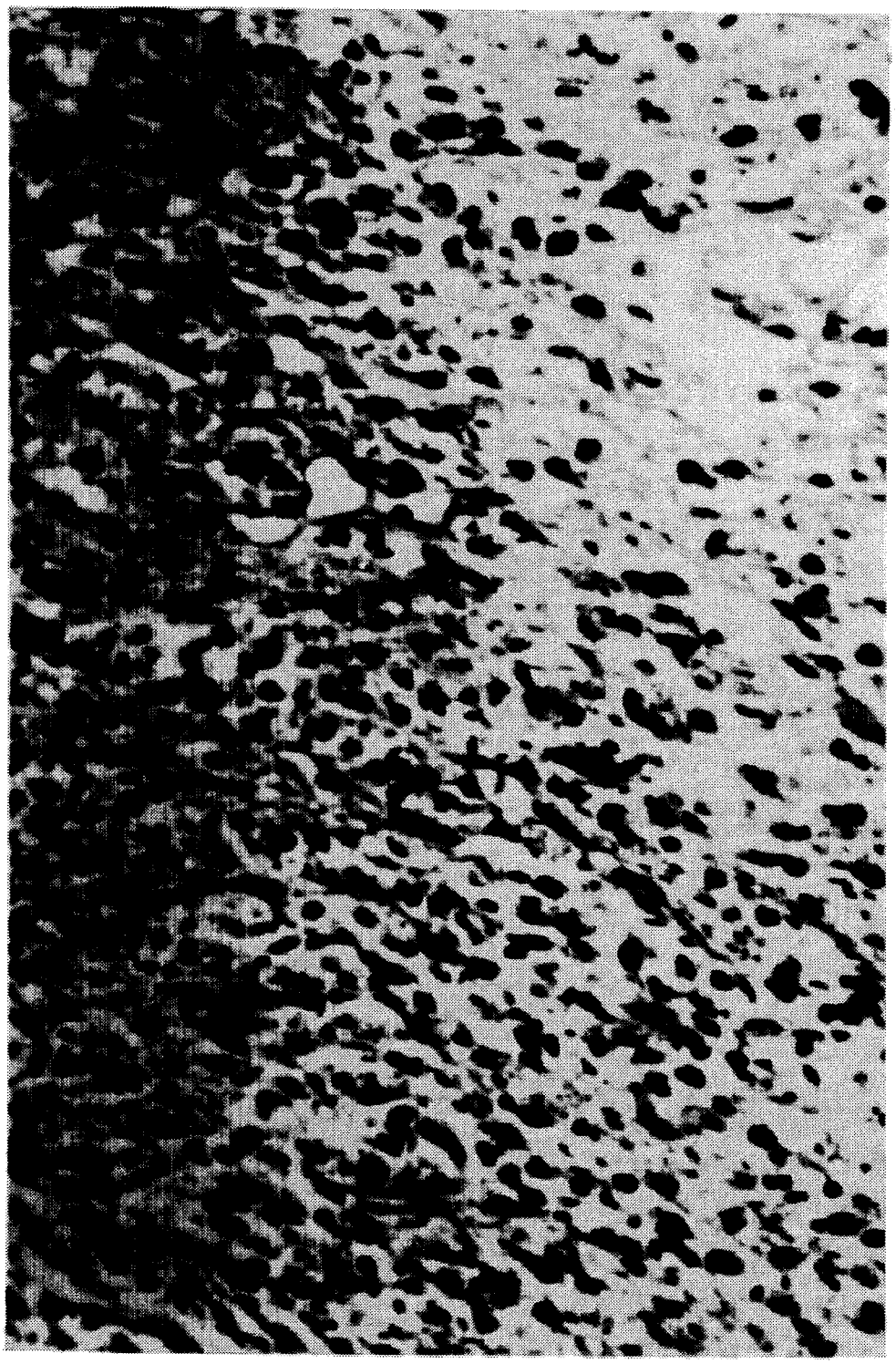

Balb/c nu/nu athymic mice were treated with either control phosphate buffered saline or SP-PG with or without oral administration (P.O.) of 1 mg tetrahydrocortisone (Sigma) in peanut oil (Sigma). Four$\times10^6$ Kaposi's Sarcoma cells were transplanted subcutaneously into the back of the mice. Angiogenic lesions (panel observed at day 6) were fixed with 4% paraformaldehyde and stained with hematoxylin-eosin (right panels). The results are shown in FIGS. 6(a) through 6(d). FIG. 6(a) shows the gross appearance and FIG. 6(c) shows the histological section of a Kaposi's Sarcoma lesion in a nude mouse after treatment with control phosphate buffered saline. FIG. 6(b) shows the gross appearance and FIG. 6(d) shows the histological section of a Kaposi's Sarcoma lesion in a nude mouse after treatment with i.v. SP-PG (5 mg) and oral tetrahydrocortisone (1 mg).

We claim:

1. A method of treating a patient with Kaposi's sarcoma comprising administration of an amount of sulfated peptidoglycan SP-PG, said amount effective to inhibit the growth of Kaposi's sarcoma lesions or to reduce edema in said patient.

2. The method of claim 1 wherein said sulfated peptidoglycan SP-PG is administered in combination with an anti-edema agent.

3. The method of claim 2 wherein said anti-edema agent is a glucocorticoid.

4. The method of claim 3 wherein said glucocorticoid is cortisone or a cortisone derivative.

5. The method of claim 4 wherein said cortisone derivative is tetrahydrocortisone.

* * * * *